United States Patent [19]

Nawata et al.

[11] Patent Number: 4,628,119
[45] Date of Patent: Dec. 9, 1986

[54] PROCESS FOR PREPARING HYDRAZINE HYDROHALOGENIDE

[75] Inventors: Takanari Nawata, Tokyo; Shuzabu Sakaguchi, Ibaraki; Osamu Aoki, Chiba, all of Japan

[73] Assignee: Mitsubishi Gas Chemical Co., Inc., Tokyo, Japan

[21] Appl. No.: 702,553

[22] Filed: Feb. 19, 1985

[30] Foreign Application Priority Data

Feb. 17, 1984 [JP] Japan .................................. 59-28323

[51] Int. Cl.$^4$ ............................................ C07C 109/04
[52] U.S. Cl. ...................................... 564/314; 564/464
[58] Field of Search ................. 564/314, 464; 423/407

[56] References Cited

U.S. PATENT DOCUMENTS 2,870,206  1/1959  Meyer .................................. 564/249
3,869,541  3/1975  Weiss et al. ......................... 423/407

FOREIGN PATENT DOCUMENTS 0126512  9/1980  Japan .................................... 423/407

OTHER PUBLICATIONS

Hayashi, H. et al, "Hydrazine Production from Ammonia via Azine" Ind. Eng. Chem., Prod. Res. Dev., vol. 15, No. 4, 1976, pp. 299–304.

*Primary Examiner*—Charles F. Warren
*Assistant Examiner*—John A. Sopp
*Attorney, Agent, or Firm*—Sughrue, Mion, Zinn, Macpeak and Seas

[57] ABSTRACT

A process for preparing hydrazine hydrohalogenide is disclosed. The process comprises the steps of:

(a) oxidizing benzophenone-imines with molecular oxygen in the presence of a copper halide catalyst to produce benzophenone-azines;

(b) contacting the oxidation reaction mixture with an aqueous solution containing a hydrohalogenic acid thereby hydrolyzing the benzophenone-azines to produce a hydrazine hydrohalogenide and, simultaneously, extracting and removing the catalyst with the hydrohalogenic acid-containing aqueous solution to obtain an aqueous solution containing the hydrazine hydrohalogenide and the catalyst;

(c) separating the aqueous solution and adjusting the solution to a pH of from 3 to 7 with an alkali;

(d) contacting the aqueous solution with benzophenone-imines to extract the catalyst;

(e) separating the catalyst-containing benzophenone-imines solution from the aqueous solution containing the hydrazine hydrohalogenide to recover the hydrazine hydrohalogenide and to recycle the catalyst-containing benzophenone-imines solution to step (a).

The process is advantageous in that the catalyst is easily recovered for reuse.

10 Claims, No Drawings

4,628,119

PROCESS FOR PREPARING HYDRAZINE HYDROHALOGENIDE

FIELD OF THE INVENTION

This invention relates to a process for preparing hydrazine hydrohalogenides comprising oxidizing benzophenone-imines with molecular oxygen in the presence of a copper halide catalyst and hydrolyzing the resulting benzophenone-azines.

BACKGROUND OF THE INVENTION

Hydrazine hydrohalogenides are industrially useful for a wide variety of applications, such as production of hydrazine, foaming agents, and the like, and, therefore, development of a process for preparing them at low cost has been demanded.

It is known that benzophenone-imines are contacted with molecular oxygen in the presence of a copper halide catalyst to obtain benzophenone-azines as described in U.S. Pat. No. 2,870,206 and that azines are hydrolyzed with an aqueous solution of a hydrohalogenic acid to obtain hydrazine hydrohalogenides as described in Japanese Patent Application (OPI) No. 97600/76 (the term "OPI" as used herein means an "unexamined published patent application").

Production of hydrazine hydrohalogenides by combining these processes is industrially advantageous but inevitably involves removal and reuse of the copper catalyst used.

Known processes for recovering the copper halide catalyst comprise adding water, aqueous ammonia or an aqueous salt solution to the reaction mixture containing the produced benzophenone-azines to precipitate the copper halide catalyst and reusing the recovered catalyst as disclosed in Japanese Patent Application (OPI) Nos. 71045/78 and 38346/80. These processes, however, cannot be considered industrially advantageous because of poor workability resulting from handling of a solid.

SUMMARY OF THE INVENTION

The present inventors have conducted extensive investigations on processes for preparing hydrazine hydrohalogenides by hydrolysis of benzophenone-azines obtained by oxidation of benzophenone-imines with molecular oxygen. As a result, it has now been found that, when benzophenoneazines are hydrolyzed by a specific process, the catalyst can not only easily be extracted and removed from the reaction mixture simultaneously with the hydrolysis but also simply and effectively be recovered from the resulting aqueous solution of hydrazine hydrohalogenide containing the catalyst and reused. The present invention has been completed based on this finding.

The present invention relates to a process for preparing a hydrazine hydrohalogenide comprising the steps of:

(a) oxidizing benzophenone-imines with molecular oxygen in the presence of a copper halide catalyst to prepare benzophenone-azines;

(b) contacting the oxidation reaction mixture obtained in step (a) with a 10 to 60 wt% aqueous solution of a hydrohalogenic acid, thereby hydrolyzing the benzophenone-azine to produce a hydrazine hydrohalogenide and, at the same time, extracting the catalyst with the hydrohalogenic acid-containing aqueous solution, to obtain an aqueous solution containing the hydrazine hydrohalogenide and the catalyst;

(c) separating the aqueous solution containing the hydrazine hydrohalogenide and catalyst which is obtained in step (b) and adjusting the solution to a pH of from 3 to 7 with an alkali;

(d) contacting the aqueous solution of pH 3 to 7 obtained in step (c) with benzophenone-imines to extract the catalyst from the aqueous solution; and (e) separating the solution containing the catalyst and the aqueous solution containing the hydrazine hydrohalogenide, thereby to recover the hydrazine hydrohalogenide as an aqueous solution and to recycle the solution containing the catalyst to step (a).

According to the present invention, hydrazine hydrohalogenides can be produced with industrial advantages in terms of easiness to recover and reuse the catalyst.

DETAILED DESCRIPTION OF THE INVENTION

The benzophenone-imines which can be used in the present invention can be represented by the formula (I):

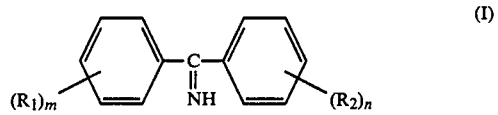

wherein $R_1$ and $R_2$, which may be the same or different, each represents an acyclic, alicyclic or aromatic hydrocarbon group having from 1 to 10 carbon atoms, an ether, acyl, acyloxy, alkoxycarbonyl, carboxylic acid amido or di-substituted amino group derived from these hydrocarbon groups, a halogen atom, a hydroxyl group, a nitro group or a cyano group, or $R_1$ and $R_2$ may be taken together to form a single bond or a ring; and m and n each represents 0 or an integer of from 1 to 5.

Specific examples of the benzophenone-imines represented by the formula (I) include benzophenone-imine, 2-, 3- or 4-methylbenzophenone-imine, 2-, 3- or 4-ethylbenzophenone-imine, 2-, 3- or 4-n- and/or isopropylbenzophenone-imine, 2-, 3- or 4-n- and/or iso- and/or tert-butylbenzophenone-imine, 2-, 3- or 4-amylbenzophenone-imine, 2-, 3- or 4-decylbenzophenone-imine, 2-, 3- or 4-methoxybenzophenone-imine, 4-cyclohexylbenzophenone-imine, 4-phenylbenzophenoneimine, 2,4-dimethylbenzophenone-imine, 2,3-dimethylbenzophenone-imine, 3,4-dimethylbenzophenone-imine, 2,4-diethylbenzophenone-imine, 2,3-diethylbenzophenone-imine, 3,4-diethylbenzophenone-imine, 2-methyl-4-ethylbenzophenone-imine, 2-methyl-4-butylbenzophenone-imine, 2,2'-, 3,3'-, 4,4'-, 2,3'-, 2,4'- or 3,4'-dimethylbenzophenone-imine, 2-, 3- or 4-chlorobenzophenoneimine, 2-chloro-4-methylbenzophenone-imine, 4-chloro-4'-methylbenzophenone-imine, 4,4'-dichlorobenzophenone-imine, 4-nitrobenzophenoneimine, 2,4-dinitrobenzophenone-imine, 4-hydroxybenzophenone-imine, 4-N,N-dimethylaminobenzophenoneimine, 4-acetylbenzophenone-imine, 4-methoxybenzophenone-imine, 4-N,N-dimethylcarbamoylbenzophenone-imine, 4-cyanobenzophenone-imine, fluorenoneimine, xanthone-imine, anthrone-imine, acridone-imine, and the like.

The imine compounds (I) to be used in the present invention have been illustrated with reference to their specific examples, but, as a matter of course, other imine compounds may also be used.

Methods for preparing these and other imines include, for example, a method of reacting corresponding benzophenones with ammonia as disclosed in U.S. Pat. No. 4,083,869, a method of reacting benzonitriles with an aryl magnesium bromide, i.e., a Grignard reagent, a method of dehydrating a diarylamino alcohol, and the like. All amines prepared by any of these methods can be employed in the present invention.

The benzophenone-imines that can be used in the present invention except for unsubstituted benzophenone-imine of the formula (I) wherein m and n are 0 are those containing various substituents or with substituents jointly forming a single bond or a ring. In carrying out the process of the invention on an industrial scale, unsubstituted benzophenone-imine and 1- or 2-mono- or 1,2-di-substituted benzophenone-imine are preferred. Among them, unsubstituted benzophenone-imine is particularly preferred.

The copper halide which can be used as a catalyst in the present invention preferably includes cuprous chloride, cuprous bromide and cuprous iodide, with cuprous chloride being more preferred.

Solvents are not particularly required in the present invention. It is possible, however, to use solvents for the purpose of maintaining the reaction system in a solution state or facilitating oil-water separation in the extraction, hydrolysis or back extraction. Such being the case, solvents that are not easily oxidized in the oxidation of benzophenone-imines and, in particular, have poor affinity for water and a low viscosity are preferred. Examples of such solvents are aromatic hydrocarbons having from 6 to 16 carbon atoms, such as benzene, toluene, o-, m- or p-xylene, ethylbenzene, mesitylene, cumene, pseudocumene, amylbenzene, etc., and mixtures of these aromatic hydrocarbons, chlorobenzene, o-, m- or p-dichlorobenzene, nitrobenzene, o-, m- or p-dinitrobenzene, o-, m- or p-chlorotoluene, diphenyl, phenanthrene, anisole, diphenyl ether, acetophenone, dibenzyl, benzophenone, hexane, heptane, cyclohexane, cyclooctane, ethylcyclohexane, ethylene dichloride, tetrachloroethylene, diisopropyl ether, dipropyl ether, diisobutyl ketone, butyl acetate, butyl benzoate, phenyl benzoate, dimethyl phthalate, and the like. Of these, benzophenone is the most preferred. It is usually preferable to use an imination reaction mixture of benzophenones as the starting benzophenone-imines, and reaction mixtures having benzophenone-imine concentrations of from 1 to 90% by weight, and preferably from 5 to 50% by weight, are usually used. In case of using the imination reaction mixture, a solvent is not always necessary since the unreacted benzophenones remaining in the reaction mixture serves as a solvent.

Each step of the process of the present invention will now be described in detail.

Step (a)

Conditions for the oxidation of benzophenone-imines are not definitely specified as varying depending on the activity and amount of the catalyst added to the reaction system, and the like, but usually, the copper halide catalyst is used in an amount ranging from $10^{-2}$ to $2 \times 10^{-1}$ mols, and preferably from $2 \times 10^{-2}$ to $10^{-1}$ mols, per liter of the total volume of the reaction solution. The reaction temperature usually ranges from 60° to 250° C., and preferably from 70° to 230° C. As molecular oxygen, air, pure oxygen and other oxygen-containing gases can be used either under atmospheric pressure or under pressure. The oxygen partial pressure is preferably from 0.01 to 20 atms., and more preferably from 0.05 to 10 atm., but wider ranges may also be used. It is desirable to control the oxidation reaction so that the conversion of imines falls within the range of from 85% to 99%.

Step (b)

In step (b), the oxidation reaction mixture obtained in step (a) is brought into contact with an aqueous solution containing a hydrohalogenic acid to thereby hydrolyze the benzophenone-azines to produce a hydrazine hydrohalogenide and, at the same time, to extract and remove the catalyst from the oxidation reaction mixture.

The hydrohalogenic acid herein used includes hydrochloric acid, hydrobromic acid and hydroiodic acid, with hydrochloric acid being preferred. Concentrations of the hydrohalogenic acid in the aqueous solution usually ranges from 10 to 60% by weight, and preferably from 20 to 40% by weight. The amount of the hydrohalogenic acid to be used is usually in the range of from 0.8 to 2 mols per mol of the benzophenone-azines subjected to the reaction. Too low amounts of the hydrohalogenic acid result in unfavorably low conversions of benzophenone-azines. On the other hand, too high amounts of the hydrohalogenic acid cause a large amount of the hydrohalogenic acid to remain unreacted in the hydrolysis reaction mixture, which leads to by-production of a large amount of salts after the subsequent neutralization.

In cases where the oxidation mixture contains unreacted benzophenone-imines, extraction and removal of the catalyst and hydrolysis of benzophenone-azines are sometimes hindered. Such being the case, it is necessary to add a hydrohalogenic acid in an amount equimolar to benzophenone-imines to be supplied in addition to the above-described amount. The temperature, pressure and oil-water contact time employed in step (b) are not particularly restricted, but usually, the temperature is from 60° to 200° C.; the pressure is from 0.1 to 10 atm.; and the contact time is from 0.1 to 10 hours.

This step can be carried out either in the presence or absence of air, and either in a batch system or in a continuous system. A counter-current multistage operation may also be employed.

Step (c)

The aqueous solution containing the hydrazine hydrohalogenide and the catalyst obtained in step (b) is separated from the hydrolysis mixture, and adjusted to a pH of from 3 to 7.

If the separated aqueous solution to be subjected to the subsequent extraction step has a pH value less than 3.0, benzophenone-imines supplied in the subsequent step are conspicuously hydrolyzed to reduce the extraction efficiency.

Therefore, it is necessary to increase the pH value of the aqueous solution up to 3 to 7 with an alkali, e.g., ammonia, sodium hydroxide, potassium hydroxide, calcium hydroxide, sodium carbonate, etc., preferably sodium hydroxide, prior to step (d).

An atmosphere for the pH-adjustment is not particularly restricted, but pH-adjustment is preferably effected in the absence of oxygen in order to avoid decomposition of hydrazines in the aqueous solution as possible. An oxygen-free atmosphere can be achieved by displacing the system with inert gases, e.g., nitrogen, helium, hydrogen, methane, ethane, carbon dioxide, etc., or steam, or by sealing the system.

Step (d)

This step comprises contacting the aqueous solution at pH 3 to 7 obtained in step (c) with benzophenone-imines to extract the catalyst.

The copper halide catalyst can easily be extracted upon contact with benzophenone-imines, and the extract is to be separated in the subsequent step (e) and recycled as a catalyst for oxidation of benzophenone-imines.

Conditions for extraction of the catalyst cannot be definitely specified as varying depending upon the concentration of the catalyst in the aqueous solution to be extracted, the type of benzophenone-imines, whether or not an organic solvent is used, the type of the aqueous solution, the mode of extraction, and the like. However, extraction can usually be conducted at a temperature of from 0° to 200° C., and preferably from 30° to 150° C., and for a period of from 1 second to 1 hour. The atmosphere employed for the extraction is the same as described in step (c).

The amount of the benzophenone-imines to be used as an extracting solvent in this step may be the whole or a part of the benzophenone-imines which are subjected to the oxidation reaction for obtaining benzophenone-azines. In the latter case, it is also possible that the concentration of the copper halide catalyst present in the benzophenone-imines which have been subjected to extraction is adjusted by addition of the benzophenone-imines which are not subjected to extraction, and the resulting benzophenone-imines solution containing the catalyst is recycled to step (a) for oxidation.

The extraction can be effected in either a batch system or a continuous system. In order to improve the extraction efficiency, counter-current multistage extraction can be appropriately adopted.

Step (e)

In this step, the extracted solution obtained in step (d) is separated into a solution of benzophenone-imines containing the catalyst and an aqueous solution containing the produced hydrazine hydrohalogenide to thereby recover the hydrazine hydrohalogenide as an aqueous solution and, at the same time, the solution of the benzophenone-imines containing the catalyst is recycled to step (a).

The hydrazine hydrohalogenide can be obtained as an aqueous solution by this step. It is also possible that the hydrazine hydrohalogenide is converted to hydrazine hydrate by addition of an alkali, followed by distillation to obtain hydrazine hydrate.

The copper halide catalyst thus recovered in an oily layer composed of the benzophenone-imines can be reused as a catalyst for the oxidation of benzophenone-imines with molecular oxygen with no need of any additional treatment.

As described above, the present invention makes it possible to recover and reuse the copper halide catalyst by easy liquid-liquid extraction without requiring any extra treatment. Thus, the present invention provides a highly rationalized process for preparing hydrazine hydrohalogenides with great industrial advantages.

The present invention will now be illustrated in greater detail with reference to an example, but it is not deemed to be limited thereto. In this example, all percents are given by weight unless otherwise indicated.

EXAMPLE 1

(1) Preparation of Benziophenone-azine by Oxidation of Benzophenone-imine

To 300 g of benzophenone-imine solution (benzophenone-imine content: 25.0%; benzophenone content: 75%; imine: 0.414 mol) was added 1.31 g (13.2 mmol) of a cuprous chloride catalyst, and the resulting mixture was stirred at 120° C. under atmospheric pressure for 2 hours while blowing oxygen gas thereinto at a rate of 0.5N l/min. After the reaction, the reaction mixture was analyzed by gas chromatography and was found to contain benzophenone-imine and benzophenone-azine at concentrations of 1.5% and 23.0%, respectively.

(2) Preparation of Hydrazine Hydrochloride by Hydrolysis of Benzophenone-azine, and Extraction of Catalyst from Oxidation Mixture of Benzophenone-imine Two hundred grams of the reaction mixture obtained in (1) above and 30.6 g of a 25% aqueous solution of hydrochloric acid (0.210 mol) were contacted at 100° C. for 2 hours under stirring to hydrolyze benzophenone-azine and, at the same time, to extract and remove the catalyst.

The rate of hydrolysis of benzophenone-azine was 92% (decomposed azine: 0.118 mol). After the reaction, the aqueous layer was analyzed and was found to contain 8.7 mmols of cuprous chloride (extractability: 99.0%) and 0.118 mol of hydrazine hydrochloride (yield: 92.0%).

(3) pH-Adjustment of Aqueous Solution Containing Hydrazine Hydrochloride and Catalyst A 40% aqueous solution of sodium hydroxide was added to the aqueous solution containing hydrazine hydrochloride and the catalyst as obtained in (2) above under a nitrogen gas stream to adjust to a pH of 5.

(4) Extraction of Catalyst with Benzophenone-Imine

The aqueous solution having been adjusted to a pH of 5 was contacted with 30 g of benzophenone-imine solution having the same composition as used in (1) above under a nitrogen gas stream at 70° C. for 30 seconds, to thereby extract cuprous chloride with the benzophenone-imine solution. This extraction operation was repeated twice.

(5) Separation of Hydrazine Hydrochloride Aqueous Solution and Preparation of Benzophenone-azine Using Catalyst Extract (Benzophenone-imine Solution)

Liquid-liquid separation after the extraction of the step (4) above gave an aqueous solution of hydrazine hydrochloride containing 0.118 mol of hydrazine hydrochloride (yield: 92.0%).

The separated catalyst extract (i.e., benzophenone-imine solution) was adjusted so as to contain 0.85 g (8.6 mmols) of cuprous chloride in 194 g of benzophenone-imine solution (benzophenone-imine content: 25.0%; benzophenone content: 75%; imine: 0.268 mol) by supplying benzophenone-imine and benzophenone. The thus adjusted solution was stirred at 120° C. under atmospheric pressure for 2 hours while blowing oxygen gas at a rate of 0.3N l/min. The reaction mixture was analyzed by gas chromatography and was found to contain 1.7% of benzophenone-imine and 23.1% of benzophenone-azine.

While the invention has been described in detail and with reference to specific embodiments thereof, it will be apparent to one skilled in the art that various changes and modifications can be made therein without departing from the spirit and scope thereof.

What is claimed is:

1. A process for preparing a hydrazine hydrohalogenide which comprises the steps of:
   (a) oxidizing a benzophenone-imine with molecular oxygen in the presence of a copper halide catalyst and benzophenone as a solvent, at a temperature of from 60° to 250° C. under an oxygen partial pressure of from 0.01 to 20 atms to produce a benzophenone-azine;
   (b) contacting the oxidation reaction mixture obtained in step (a) with a 10 to 60 wt% aqueous solution of a hydrohalogenic acid in an amount of from 0.8 to 2 moles per mole of the benzophenone-azine at a temperature of from 60° to 200° C. under a pressure of from 0.1 to 10 atms, thereby hydrolyzing the benzophenone-azine to produce a hydrazine hydrohalogenide and, at the same time, extracting and removing the catalyst from the reaction mixture with the hydrohalogenic acid-containing aqueous solution, to obtain an aqueous solution containing the hydrazine hydrohalogenide and the catalyst;
   (c) separating the aqueous solution containing the hydrazine hydrohalogenide and catalyst which is obtained in step (b) and adjusting the solution to a pH of from 3 to 7 with an alkali in the absence of oxygen;
   (d) contacting the aqueous solution of pH 3 to 7 obtained in step (c) with benzophenone-imines at a temperature of from 0° to 200° C. in the absence of oxygen to extract the catalyst from the aqueous solution with the benzophenone-imines; and
   (e) separating the benzophenone-imines solution containing the catalyst and the aqueous solution containing the hydrazine hydrohalogenide, to thereby recover the hydrazine hydrohalogenide as an aqueous solution and to recycle the solution containing the catalyst to step (a).

2. A process as claimed in claim 1, wherein the copper halide catalyst in step (a) is cuprous chloride.

3. A process as claimed in claim 1, wherein the copper halide catalyst is present at a concentration of from $10^{-2}$ to $2 \times 10^{-1}$ mol per liter of the total volume of the reaction solution.

4. A process as claimed in claim 1, wherein said benzophenone-imine in step (a), (d) or (e) is benzophenone-imine and said benzophenone-azines in step (a) or (b) is benzophenone-azine.

5. A process as claimed in claim 1, wherein step (a) is conducted while controlling the benzophenone-imine conversion within a range of from 85% to 99%.

6. A process as claimed in claim 1, wherein the aqueous solution of a hydrohalogenic acid in step (b) contains a hydrohalogenic acid at a concentration of from 20 to 40% by weight.

7. A process as claimed in claim 1, wherein the oxidation reaction mixture obtained in step (a) contains the unreacted benzophenone-imine and the hydrohalogenic acid in step (b) is used in a total amount of an equimole to the unreacted benzophenone-imine and from 0.8 to 2 mols per mole of the benzophenone-azine.

8. A process as claimed in claim 1, wherein the hydrohalogenic acid in step (b) is hydrochloric acid.

9. A process as claimed in claim 1, wherein the alkali in step (c) is ammonia, sodium hydroxide, potassium hydroxide, calcium hydroxide or sodium carbonate.

10. A process as claimed in claim 1, wherein the alkali in step (c) is sodium hydroxide.

* * * * *